(12) United States Patent
Brechbiel et al.

(10) Patent No.: US 8,288,530 B2
(45) Date of Patent: Oct. 16, 2012

(54) METHOD OF PREPARING MACROMOLECULAR CONTRAST AGENTS AND USES THEREOF

(75) Inventors: Martin W. Brechbiel, Annandale, VA (US); Heng Xu, Rockville, MD (US)

(73) Assignee: The United States of America, as represented by the Department of Health and Human Services, Washington, DC (US)

( * ) Notice: Subject to any disclaimer, the term of this patent is extended or adjusted under 35 U.S.C. 154(b) by 583 days.

(21) Appl. No.: 12/513,813

(22) PCT Filed: Nov. 6, 2007

(86) PCT No.: PCT/US2007/083734
§ 371 (c)(1), (2), (4) Date: Jun. 3, 2009

(87) PCT Pub. No.: WO2008/070384
PCT Pub. Date: Jun. 12, 2008

(65) Prior Publication Data
US 2010/0056776 A1    Mar. 4, 2010

Related U.S. Application Data

(60) Provisional application No. 60/864,503, filed on Nov. 6, 2006.

(51) Int. Cl.
*C07D 403/12* (2006.01)
*C07D 207/46* (2006.01)
*C07D 207/40* (2006.01)
*C07D 257/02* (2006.01)
*C07C 229/00* (2006.01)

(52) U.S. Cl. ........... 540/474; 548/542; 548/546; 560/37

(58) Field of Classification Search .................. None
See application file for complete search history.

(56) References Cited

U.S. PATENT DOCUMENTS

| | | |
|---|---|---|
| 5,124,471 A | 6/1992 | Gansow et al. |
| 5,246,692 A | 9/1993 | Gansow et al. |
| 5,286,850 A | 2/1994 | Gansoh et al. |
| 5,434,287 A | 7/1995 | Gansow et al. |
| 7,081,452 B2 | 7/2006 | Brechbiel et al. |

FOREIGN PATENT DOCUMENTS

| | | |
|---|---|---|
| WO | WO 00/51976 A1 | 9/2000 |
| WO | WO 03/014157 A2 | 2/2003 |
| WO | WO 2004/021996 A2 | 3/2004 |
| WO | WO 2006/033714 A2 | 3/2006 |

OTHER PUBLICATIONS

Ahrends et al., Molecular & Cellular Proteomics 6.11, 2007, 1907-1916.*
Anelli et al., "L-Glutamic acid and L-lysine as useful building blocks for the preparation of bifunctional DTPA-like ligands," *Bioconjug Chem.*, 10(1), 137-140 (1999).
Brechbiel et al., "Backbone-substituted DTPA ligands for $^{90}Y$ Radioimmunotherapy," *Bioconjug. Chem.*, 2, 187-194 (1991).
Brechbiel et al., "Purification of p-nitrobenzyl C-functionalized diethylenetriamine pentaacetic acids for clinical applications using anion-exchange chromatography," *J. Chromatogr. A*, 771, 63-69 (1997).
De Luca et al., "Synthesis and characterization of a sulfated and a non-sulfated cyclic CCK8 analogue functionalized with a chelating group for metal labelling," *J Pept Sci.*, 10 (5), 265-273 (2004).
Hnatowich et al., "Radioactive labeling of antibody: a simple and efficient method," *Science*, 220, 613-615 (1983).
Krejcarek et al., "Covalent attachment of chelating groups to macromolecules," *Biochem. Biophys. Res. Commun.*, 77 (2), 581-585 (1977).
Milenic et al., "Antibody-targeted radiation cancer therapy," *Nature Reviews Drug Discovery*, 3, 488-499 (2004).
Wu et al., "Stereochemical influence on the stability of radio-metal complexes in vivo. Synthesis and evaluation of the four stereoisomers of 2-(p-nitrobenzyl)-*trans*-CyDTPA," *Bioorg. Med. Chem. Lett.*, 5 (10), 1925-1934 (1997).
Yordanov et al., "Gadolinium-labeled dendrimers as biometric nanoprobes to detect vascular permeability," *J. Mater. Chem.*, 13, 1523-1525 (2003). Wang et al., "Convenient solid-phase synthesis of diethylenetriaminepenta-acetic acid (DTPA)—conjugated cyclic RGD peptide analogues," *Cancer Biother Radiopharm.*, 20 (5), 547-556 (2005).

* cited by examiner

*Primary Examiner* — Sun Jae Loewe
(74) *Attorney, Agent, or Firm* — Leydig, Voit & Mayer, Ltd.

(57) ABSTRACT

Disclosed are methods of preparing a macromolecular conjugated ligand and a metal complex thereof. The metal complex is targeted for use as a contrast agent, for example, in MRI. The method of preparing a macromolecular conjugated ligand comprises: (a) providing a compound of formula (I)

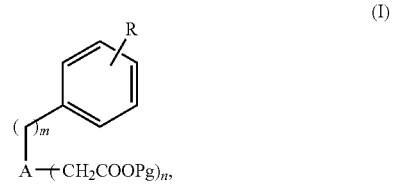

wherein R, A, and Pg are as defined herein, (b) reacting the compound of formula (I) with a macromolecular compound (e.g., dendrimer) in an organic solvent medium which is substantially free of water to obtain a macromolecular conjugated compound, and (c) removing the carboxyl-protecting groups to obtain a carboxyl-deprotected macromolecular conjugated compound. The metal complex can be prepared by reacting the carboxyl-deprotected macromolecular conjugated compound with an ion (e.g., Gd(III)). Also disclosed are two carboxyl-protected 1B4M-DTPA intermediate compounds.

28 Claims, 4 Drawing Sheets

METHOD OF PREPARING MACROMOLECULAR CONTRAST AGENTS AND USES THEREOF

CROSS-REFERENCE TO RELATED APPLICATIONS

This patent application claims the benefit of U.S. Provisional Patent Application No. 60/864,503, filed Nov. 6, 2006, which is incorporated by reference.

BACKGROUND OF THE INVENTION

The development of contrast agents for magnetic resonance imaging (MRI) in clinical settings continues to receive great attention (Merbach et al., The Chemistry of Contrast Agents in Medical Magnetic Resonance Imaging. John Wiley & Sons: New York, 2001). Paramagnetic metal chelates, such as Gd(III)-diethylenetriaminepentaacetic acid (Gd(III)-DTPA) (Magnevist), Gd(III)-N,N',N',N'',N'''-tetracarboxymethyl-1,4,7,10-tetraazacyclododecane (Gd(III)-DOTA), and their analogs have proven to increase the relaxation rate of surrounding protons and have been widely used as MRI contrast agents (Lauffer, Chem. Rev., 1987, 87, 901-927 and Caravan et al., Chem. Rev., 1999, 99, 2293-2352). However, these low molecular weight agents have disadvantages such as rapid circulation and clearance rates in vivo, and relatively low molar relaxivity properties thus limiting time-dependent imaging studies or acquisition of highly resolved images of patients (Kobayashi et al., Adv. Drug Deliv. Rev., 2005, 2271-2286; Comblin et al., Coord. Chem. Rev., 1999, 186, 451-470; and Raymond et al., Bioconjugate Chem., 2005, 16, 3-8).

Attempts have been made to develop bifunctional chelates as imaging agents. Such attempts have led to the establishment of a library such as 2-(4-isothiocyanatobenzyl)-6-methyl-diethylenetriamine pentaacetic acid (1B4M-DTPA), N-[2-amino-3-(4-isothiocyanatobenzyl)propyl]-cis-cyclohexyl-1,2-diamine-N,N',N',N'',N''-pentaacetic acid (CHX-A-DTPA), and 2-(4-isothiocyanatobenzyl)-1,4,7,10-tetraazacyclododecane-N,N',N'',N'''-tetraacetic acid (p-SCN-Bz-DOTA), that are potentially useful for forming Gd(III) complexes and thus MRI contrast agents (Brechbiel et al., Bioconjug. Chem., 1991, 2, 187-194 and Wu et al., Bioorg. Med. Chem. Lett., 1997, 5, 1925-1934). The bifunctional chelators permit, on the one hand, conjugation to biomolecules such as, antibodies and peptides, dendrimers, and other macromolecular structures (Milenic et al., Nature Reviews Drug Discovery, 2004, 3, 488-499), and chelation to metal ions, on the other hand.

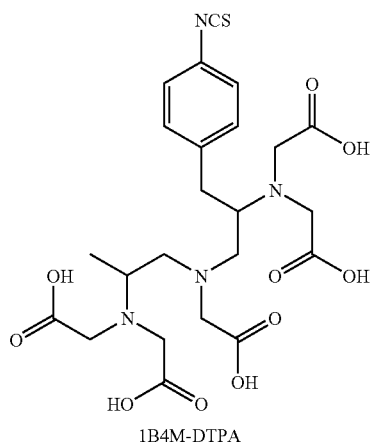

1B4M-DTPA

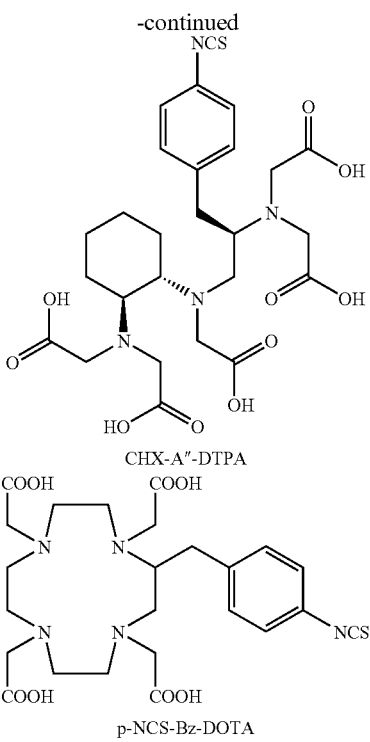

CHX-A''-DTPA p-NCS-Bz-DOTA

The synthetic methods attempted in the past to prepare macromolecular conjugated bifunctional chelators have one or more drawbacks such as the use of large excess of reagents or the need to carry out extensive purification from impurities formed in the conjugation reaction.

Thus, there is a desire for an improved synthesis of macromolecular-based magnetic resonance agents.

BRIEF SUMMARY OF THE INVENTION

The invention provides a synthetic approach of a metal chelate based on a multidentate polyamino ligand having one or more carboxymethyl groups, such as 2-(4-isothiocyanatobenzyl)-6-methyl-diethylenetriamine pentaacetic acid (1B4M-DTPA), that is conjugated to a biomolecule (e.g., antibody or peptide) or dendrimer. In particular, the synthesis provides an improvement in overall efficiency of bifunctional chelator binding to poly-amine surface dendrimers by elimination of loss of the reagent to aqueous basic pH conditions, shorter reaction times, and a potential increase in loading efficiency of chelator onto the macromolecular structure. Specifically, the synthesis of a conjugate complex includes the following steps: (a) preparation of a protected multidentate polyamino ligand having one or more carboxymethyl groups, (b) conjugation to a macromolecular structure (e.g., dendrimer) in an organic solvent, (c) deprotection of the carboxylic acid groups, and (d) complexation with a metal (e.g., Gd(III)). Advantageously, elimination or delay of using an aqueous solvent helps improve the overall efficiency of conjugation and reduces possible contamination by spurious metals that could compromise the radiolabeling and/or metal complexation in step (d).

BRIEF DESCRIPTION OF THE SEVERAL VIEWS OF THE DRAWING(S)

DETAILED DESCRIPTION OF THE INVENTION

Figure 1:
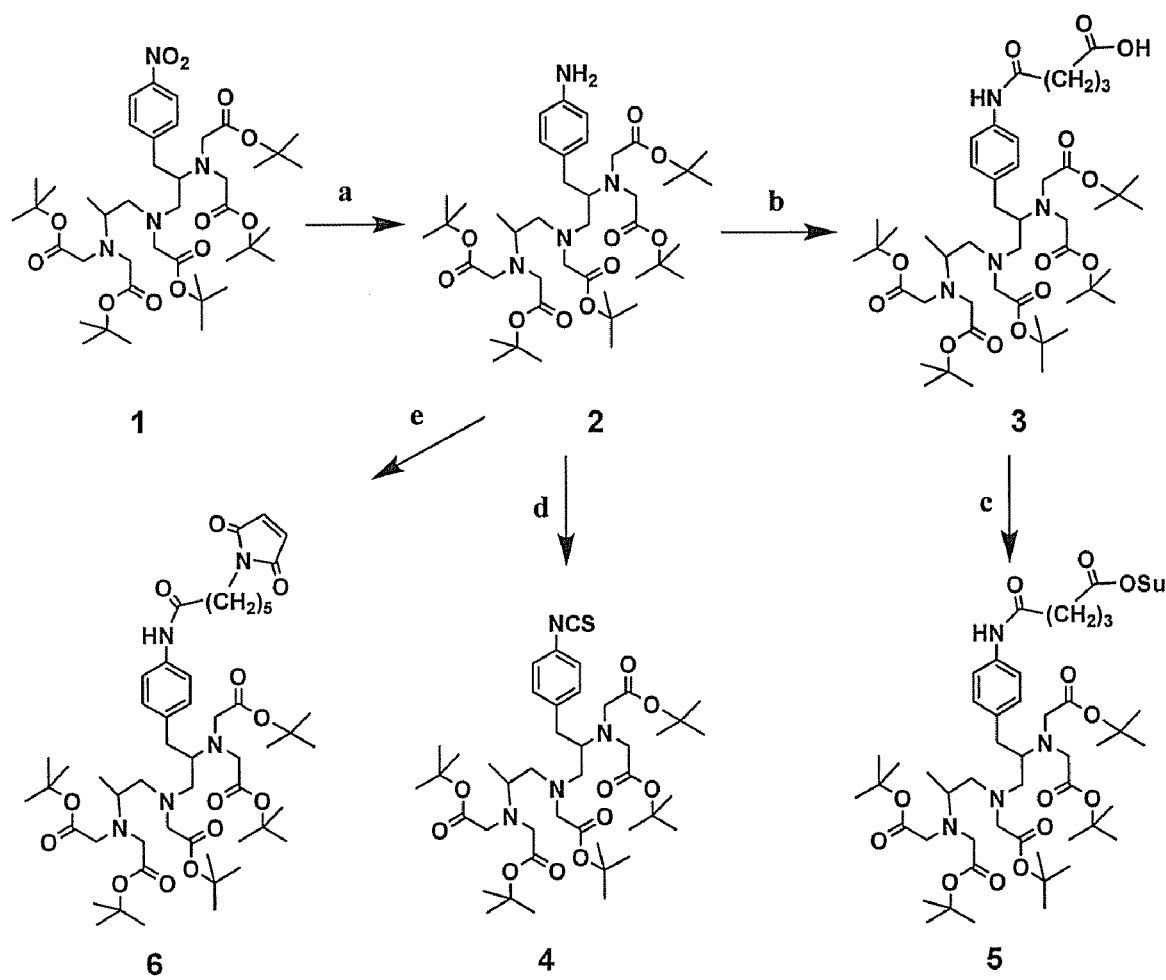
FIG. 1 illustrates a method of preparing protected 1B4M-DTPA compounds, in accordance with an embodiment of the invention. The reaction conditions are: (a) H$_2$, 10% Pd/C, EtOH, 96%; (b) glutaric anhydride, EtOAc, 82%; (c) EDCI, NHS, MeCN, 88%; (d) ClCSCl, EtOAc, 96%; and (e) N-maleimidocaproic acid, EDCI, CH$_2$Cl$_2$, 84%.

The present invention provides, in an embodiment, a method of preparing a macromolecular conjugated ligand comprising:

(a) providing a compound of formula (I)

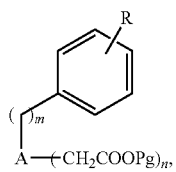

(I)

wherein
A is a polyamino group,
R is hydrogen, halo, allyl, hydroxy, nitro, amino, alkylamino, dialkylamino, thiocyano, isothiocyano, carboxyl, carboxyalkyl, carboxyalkyloxy, amido, alkylamido, haloallylamido,

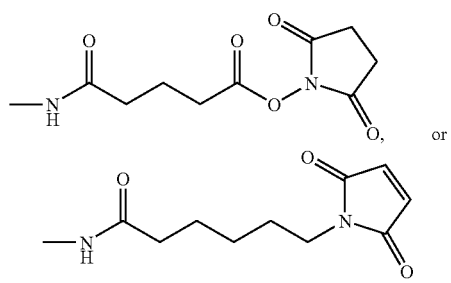

Pg is a carboxyl-protecting group,
n is 1 to 5, and m is 0 to 3,
(b) reacting the compound of formula (I) with a macromolecular compound in an organic solvent medium which is substantially free of water to obtain a carboxyl-protected macromolecular conjugated ligand, and (c) removing the carboxyl-protecting group to obtain a macromolecular conjugated ligand.

The method can further comprise step (d), wherein step (d) comprises reacting the macromolecular conjugated ligand with an ion (e.g., a metal or non-metal ion), which is optionally radioactive, to obtain a macromolecular conjugated ligand complex.

The polyamino group A is a polyallyleneimine group and is cyclic (e.g., together with carboxymethyl groups, DOTA, 1,4,7-triazacyclononane-N,N',N''-triacetic acid (NOTA)) or acyclic (e.g., together with carboxymethyl groups, DTPA). Examples of A, together with carboxymethyl groups, are described in WO 04/021996 and U.S. Pat. Nos. 7,081,452, 5,434,287, 5,286,850, 5,246,692, and 5,124,471, which are incorporated herein by reference. The number of carboxymethyl groups varies depending on the structure and number of amino moieties. For this reason, n is 1 to 5 (e.g., 1, 2, 3, 4, or 5). Typically for DOTA and DTPA moieties, n is 4 or 5, respectively. The backbones of the polyamino cyclic or acyclic ligand can be substituted with, for example, alkyl (e.g., methyl), cycloalkyl (e.g., cyclohexyl), or heterocycloalkly (e.g., piperidinyl). The backbone substituents can be any suitable stereochemistry, such as cis or trans, (e.g., trans-cyclohexyl). In an embodiment, the polyamino group A together with $-(CH_2COOPg)_n$ can be a compound of formula (II) or (III):

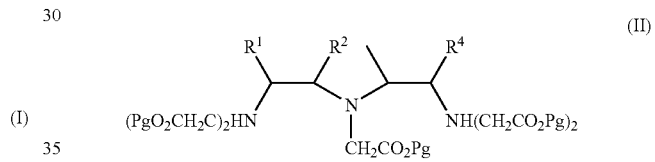

(II)

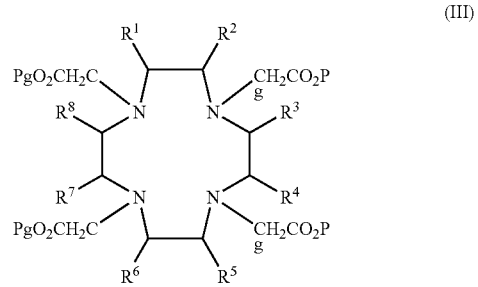

(III)

wherein R$^1$-R$^8$ is hydrogen, a C$_1$-C$_{12}$ alkyl group, or a point of attachment of

 or

R$^1$ and R$^2$ or R$^3$ and R$^4$ together form a C$_5$-C$_7$ cycloalkyl group.

In an embodiment of the invention, -A$-$(CH$_2$COOPg)$_n$ can be, for example, 6-methyl-diethylenetriamine pentaacetic acid (a), cyclohexyl-1,2-diamine-N,N',N',N'',N''-pentaacetic acid (b), or 1,4,7,10-tetraazacyclododecane-N,N',N'',N'''-tetraacetic acid (c).

a

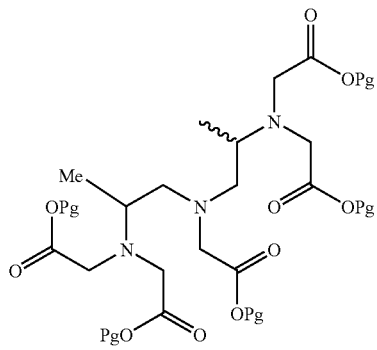

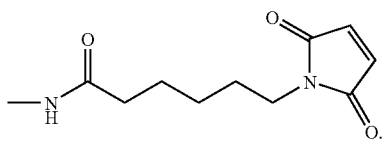

Preferably, R is isothiocyanato (—NCS),

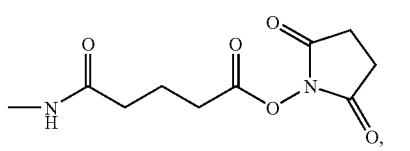

or b

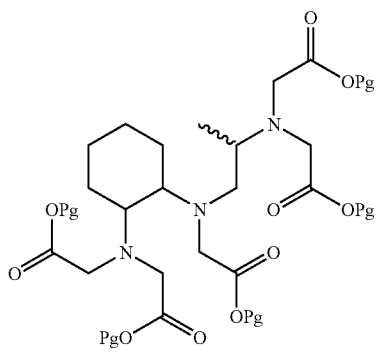

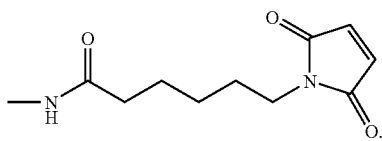

The substituent R can be at any suitable position on the phenyl ring relative to the remainder of the molecule (e.g., ortho, meta, para). Preferably, R is para to the remainder of the molecule. The substituent m is 0 to 3 (e.g., 0, 1, 2, or 3). The value of m depends on the specific structure of formula (I) and can be varied for ease of conjugation to the macromolecular compound. Preferably m is 1.

c

In an embodiment of the invention, the compound of formula (I) is

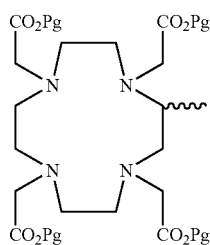

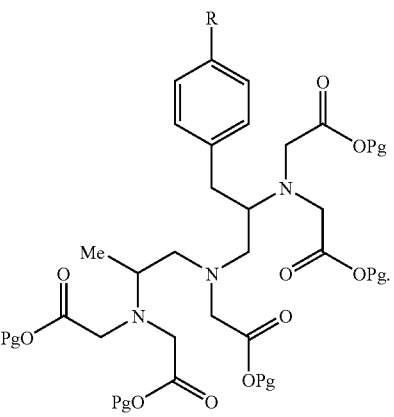

R is selected from the group consisting of hydrogen, halo, allyl, hydroxy, nitro, amino, allylamino, dialkylamino, thiocyano, isothiocyano, carboxyl, carboxyallyl, carboxyallyloxy, amido, allylamido, haloalkylamido,

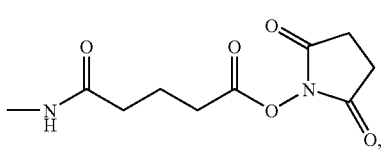

and

In a specific embodiment, a compound of formula (I) includes a compound of formula (Ia), (Ib), (Ic), (Id), (Ie), and/or (If):

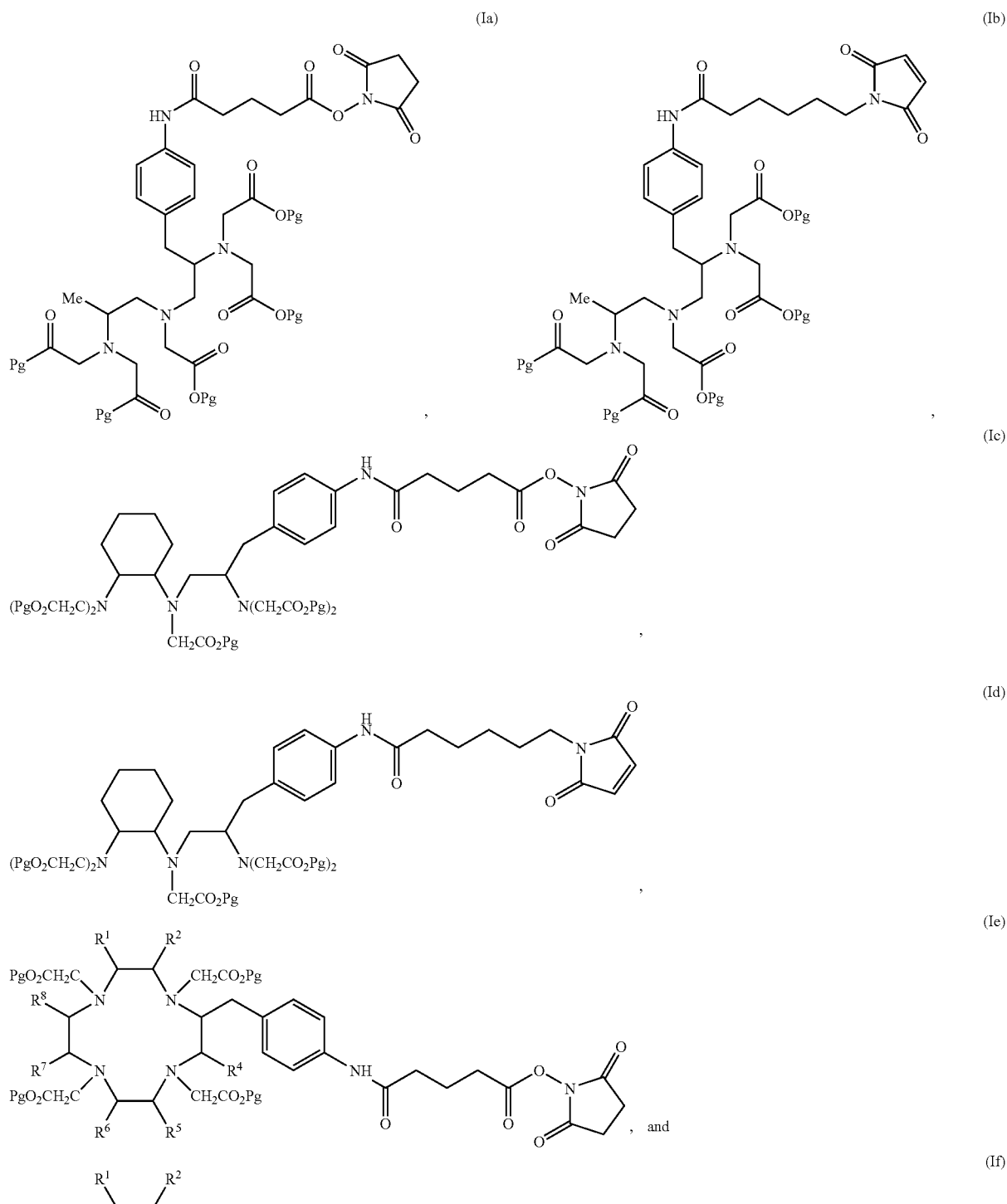
wherein Pg is a carboxyl-protecting group.

In the compound of formula (I), (Ia), (Ib), (Ic), (Id), (Ie), and/or (If), the protecting group, Pg, is any suitable carboxylic acid protecting group. Typically Pg forms an ester with the carboxylate functional group. For example, suitable moieties for Pg include alkyl (e.g., methyl, t-butyl), benzyl, 9-fluorenylmethyl, diphenylmethyl, silylallyl, haloallyl, and 1,1-dimethylallyl (DMA). Preferably, Pg is an alkyl, such as t-butyl.

The protecting group can be added to the -A—$(CH_2COOPg)_n$ group (e.g., DTPA) by any suitable method known in the art. For example, alkyl esters can be formed by Fisher esterification, addition of acid chloride and alcohol, addition of isobutylene and acid, or addition of diazomethane. Use of a coupling agent, such as dicyclohexylcarbodiimide (DCC) (*Tetrahedron Letters*, 1983, 24, 281) is a common method of forming protected carboxylic acids (e.g., 9-fluorenylmethyl esters, haloesters, 2-(trimethylsilyl)ethyl esters, benzyl esters, and diphenylmethyl esters). DMA esters can be formed using procedures known in the art. See, for example, Sedighi et al., *Organic Letters*, April 2006, 7(8), 1473-1475.

When necessary, the protecting group can be removed by any suitable method known in the art, which method typically includes addition of acid, base or an organometallic reagent (e.g., magnesium bromide), enzymatic hydrolysis (e.g., pig liver esterase), hydrogenolysis, reduction, or addition of dibutyltin oxide. Any suitable acid or base can be used, including trifluoroacetic acid, HCl, $H_2SO_4$, $H_3PO_4$, NaOH, KOH, or LiOH. For example, for the cleavage of 9-fluorenylmethyl, addition of a mild base (e.g., diethylamine, piperidine, or ammonia) is preferred. For hydrogenolysis, conditions such as addition of hydrogen gas in the presence of a catalyst (e.g., palladium on carbon) can be used. Silylallyl esters can be cleaved, for example, with fluoride ion. Haloesters can be removed, for example, with Zn(0) dust or electrochemically. Diphenylmethyl esters can be cleaved, for example, with boron trifluoride. Additional protecting group and methods of addition and removal are discussed in T. W. Greene et al. *Protective Groups in Organic Synthesis* ($2^{nd}$ Ed.) J. Wiley and Sons, 1991, which is incorporated by reference.

The term "allyl" means a straight-chain or branched alkyl substituent containing from, for example, 1 to about 12 carbon atoms, preferably from 1 to about 8 carbon atoms, more preferably from 1 to about 6 carbon atoms. Examples of such substituents include methyl, ethyl, propyl, isopropyl, n-butyl, sec-butyl, isobutyl, t-butyl, pentyl, isoamyl, hexyl, octyl, dodecanyl, and the like, preferably t-butyl.

The term "halo" as used herein, means a substituent selected from Group VIIA of the Periodic Table of Elements, such as, for example, fluorine, bromine, chlorine, and iodine. Preferably, the halo is bromine or iodine.

The term "haloalkyl," as used herein, means an alkyl substituent that is bonded to at least one halo as described herein. The allyl group of haloalkyl is as described above.

The term "allylamino" refers to a secondary amine substituent with one hydrogen and one alkyl group directly attached to a trivalent nitrogen atom. The term "diallylamino" refers to a tertiary amine substituent with two of the same or different alkyl groups directly attached to a trivalent nitrogen atom. The allyl group is described above.

The term "carboxyl" refers to the group —C(O)OH. The term "carboxyalkyl" refers to the group —R'C(O)OH that is connected to the compound through the alkyl R' group. The term "carboxyallyloxy" refers to the group —OR'C(O)OH, in which the R' is an allyl (e.g., $(CH_2)_n$ allylene group, n is 1 to 12) group. The alkyl group is described above.

The term "allylamido" refers to substituents of the formula, —C(O)NRR' or —NR'C(O)R", in which R' and R" are the same or different and each is a hydrogen or alkyl group, as described above. The term "haloallylamido" is an allylamido, in which one or more of the allyl groups is substituted with a halo moiety as described above, such as, for example, chlorine, bromine or iodine.

The term "silylallyl" as used herein, means one, two, or three alkyl groups (the same or different) as defined herein, directly attached to a tetravalent silicon atom. Examples of such substituents include, for example, trimethylsilyl, methyl (dibutyl)silyl, tri-iso-propylsilyl, and the like.

The compound of formula (I) (which includes compounds of formula (Ia), (Ib), (Ic), (Id), (Ie), and/or (If)) can be conjugated to any suitable macromolecular compound, e.g., biomolecule or a dendrimer. The term "biomolecule" refers to all natural and synthetic molecules that play a role in biological systems. A biomolecule includes a hormone, an amino acid, a peptide, a peptidomimefic, a protein, deoxyribonucleic acid (DNA), ribonucleic acid (RNA), a lipid, an albumin, a polyclonal antibody, a receptor molecule, a receptor binding molecule, a hapten, a monoclonal antibody and an aptamer. Specific examples of biomolecules include insulins, prostaglandins, growth factors, liposomes and nucleic acids. An advantage of using biomolecules could be tissue targeting through specificity of delivery. Another advantage could be longer residence time.

Haptens such as hormones, steroids, enzymes and proteins are desirable in some applications because of their site specificity to tumors and/or various organs of the body. A preferred hapten for use in treating cellular disorders or various disease conditions is a monoclonal antibody. Methods of bonding a macrocyclic compound to a hapten are described in U.S. Pat. No. 5,428,154, which are incorporated herein by reference.

Coupling of a compound of formula (I) to one or more macromolecular compounds can be accomplished by several known methods (see, for example, Krejcarek et al., *Biochem. Biophys. Res. Commun.*, 1977, 30, 581; and Hnatowich et al., *Science*, 1983, 220, 613). For example, a reactive moiety present in the R substituent is coupled with a second reactive group located on the macromolecule. Typically, a nucleophilic group on the macromolecule is reacted with an electrophilic group on the compound of formula (I) to form a covalent bond between the two. Examples of nucleophilic groups include amines, anilines, alcohols, phenols, thiols and hydrazines.

The dendrimer refers to a synthetic, three dimensional molecule with branching parts. The branches are built up from monomers. The dendrimers are typically made by a nanoscale fabrication process compound suitable for conjugation to a compound of formula (I). Unlike classical polymers, dendrimers have a high degree of molecular uniformity, narrow molecular weight distribution, specific size and shape characteristics, and a highly-functionalized terminal surface. The manufacturing process is a series of repetitive steps starting with a central initiator core. Each subsequent growth step represents a new "generation" of polymer with a larger molecular diameter, twice the number of reactive surface sites, and approximately double the molecular weight of the preceding generation. Suitable dendrimers include polyamidoamine (PAMAM) dendrimers, polypropylenimine (PPI) dendrimers, and those described in the literature, such as U.S. Pat. Nos. 4,289,872, 4,410,688, and 4,507,466, Tomalia et al., *Polymer Journal*, 1985, 17(1), 117-132, and Jiang et al., *Nature*, 1997, 388, 454-456. PAMAM dendrimers, which are preferred, represent a class of macromolecular architecture called "dense star" polymers. Suitable conjugation methods of a dendrimer and a compound of formula (I) are described herein and are also known in the art. See, for example, U.S. Pat. No. 5,527,524, the entirety of which is incorporated herein.

When conjugating the compound of formula (I) to a dendrimer, typically an excess of compound compared to dendrimer is used. For example, typically at least a 2:1 (e.g., 2.2:1, 2.5:1, 2.8:1, 3:1, 4:1, 5:1) functional ratio of compound to dendrimer is used. For most applications, a 2:1 ratio is preferred. A large excess of the compound of formula (I) is not required for step (b) of the inventive method, which can simplify the reaction monitoring process and purification step(s) since organic by-products and inorganic salts, which can be major components of the crude reaction solution, are minimized.

The conjugation reaction (i.e., step (b) of the inventive method) is carried out in a medium comprising at least one organic solvent that is free or substantially free of water, such as an alkane, an aromatic hydrocarbon, a haloalkane, an alcohol, an amide, an alkylester, a sulfoxide, a cycloalkane, a dialkylether, an allyl aryl ether, a diarylether, and a cyclic ether. Specific organic solvents that are suitable include acetonitrile, dimethylformamide (DMF), benzene, methylene chloride, methanol, hexane, dimethylsulfoxide (DMSO), tetrahydrofuran (THF), furan, diphenyl ether, diethyl ether, methylethyl ether, and dioxane or any combination thereof. Preferred solvents include methanol and DMSO. The term "substantially free of water" means an organic solvent that contains less than 5% by wt. water (e.g., less than 4% by wt. water, less than 3% by wt. water, less than 2% by wt. water, less than 1% by wt. water, less than 0.5% by wt. water, less than 0.25% by wt. water).

If necessary, water can be used during steps of the inventive method other than the conjugation step. For example, to minimize any possible complications associated with removal of a high boiling point solvent (e.g., DMSO), crude conjugated compounds of formula (I) can be diluted with a first solvent (e.g., $CH_2Cl_2$) and then washed with water to remove the high boiling solvent. Reduction, elimination or delay of using an aqueous solvent in the synthesis helps improve the overall efficiency of conjugation.

The carboxyl-deprotected conjugated compound of formula (I) can be complexed to an ion, e.g., a metal ion or a non-metal ion, in which the ion is optionally radioactive. Typical metal ions for forming a complex of the invention include Ac, Bi, Pb, Y, Mn, Cr, Fe, Co, Ni, Tc, In, Ga, Cu, Re, a lanthanide (i.e., any element with atomic number 57 to 71 inclusive, such as Sm), and an actinide (i.e., any element with atomic number 89 to 103 inclusive). The metal ion is any metal ion that is suitable for the desired end use of the complex. For example, in proton magnetic resonance imaging, paramagnetic metal atoms such as gadolinium(III), manganese(II), manganese(III), chromium(III), iron(II), iron(III), cobalt(II), nickel(II), copper(II), praseodymium(III), neodymium(III), samarium(III), ytterbium(III), terbium(III), dysprosium(III), holmium(III), and erbium(III) (all are paramagnetic metal atoms with favorable electronic properties) are preferred as metals complexed by the carboxyl-deprotected conjugated compound. Gadolinium(III) is a further preferred complexed metal due to the fact that it has high paramagnetism, low toxicity when complexed to a suitable ligand, and high lability of coordinated water. For use as x-ray contrast agents, the metal ion should be able to absorb an adequate amount of x-rays (i.e., radio-opaque), such as, for example, indium, yttrium, lead, bismuth, gadolinium, dysprosium, holmium and praseodymium.

The carboxyl-deprotected conjugated compound of formula (I) also can be complexed with a radioactive ion, such as a radioactive metal ion, for use as a therapeutic agent (e.g., a radiopharmaceutical). Radioisotopes of any suitable ion are acceptable for forming metal or other ion complexes. For example, typical radioisotopes include isotopes of technetium, bismuth, lead, actinium, carbon, nitrogen, iodine, fluorine, oxygen, tellurium, helium, indium, gallium, copper, rhenium, yttrium, samarium and holmium. A radioactive isotope of yttrium is preferred. Specific examples of radionuclides suitable for complexing to a carboxyl-deprotected conjugated compound for various imaging techniques, including positron emission tomography and single photon emission computed spectroscopy, are, for example, $^{86}Y$, $^{213}Bi$, $^{212}Bi$, $^{212}Pb$, $^{225}Ac$, $^{177}Lu$, $^{99m}Tc$, $^{111}In$, $^{11}C$, $^{13}N$, $^{123}I$, $^{186}Re$, $^{18}F$, $^{15}O$, $^{201}Tl$, $^{3}He$, $^{166}Ho$ and $^{67}Ga$, preferably $^{86}Y$, and $^{111}In$.

To prepare metal complexes of the invention, the carboxyl-deprotected conjugated compound of formula (I) is complexed with an appropriate atom or ion, e.g., metal or metal ion. This can be accomplished by any methodology known in the art. For example, the metal can be added to water in the form of an oxide, halide, nitrate or acetate (e.g., yttrium acetate, bismuth iodide) and treated with an equimolar amount of the carboxyl-deprotected macromolecular conjugated compound of formula (I). The compound can be added as an aqueous solution or suspension. Dilute acid or base can be added (where appropriate) to maintain a suitable pH. Heating at temperatures as high as 100° C. for periods of up to 24 hours or more can be employed to facilitate complexation, depending on the metal, the compound, and their concentrations.

The macromolecular conjugated complexes prepared by the inventive method can be used for obtaining a diagnostic image of a host. In such methods, typically the host is administered a complex, in an amount effective to provide an image; and the host is exposed to an energy source, whereupon a diagnostic image of the host is obtained. The diagnostic image can be, for example, a magnetic resonance image (MRI), an x-ray contrast image, positron emission tomography (PET), single photon emission computed spectroscopy (SPECT) image, or the like.

The macromolecular conjugated complexes prepared by the inventive method can be used for treating a cellular disorder, such as cancer, in a mammal. The method comprises administering to the mammal (e.g., a human) a complex of the present invention in an amount effective to treat the cellular disorder, whereupon the cellular disorder is treated. A preferred complex comprises Pb or Y, in particular $^{90}Y$.

The following examples further illustrate the invention but, of course, should not be construed as in any way limiting its scope.

EXAMPLES

Materials and Methods: 2-Methyl-6-(p-nitrobenzyl)diethylene-N,N,N',N'',N''-penta-tert-butylacetate (1) is prepared by modification of the previously described procedure (Brechbiel et al., *J. Chromatogr., A,* 1997, 771, 63-69). N-hydroxysuccinimide (NHS), 1-[3-(dimethylamino)propyl]-3-ethylcarbodiimide hydrochloride (EDCI), thiophosgene, glutaric anhydride, and peptide sequence grade trifluoroacetic acid are purchased from Aldrich/Sigma Chemical Company and are used as received. Generation 4 ethylenediamine core PAMAM dendrimers are obtained from Dendritech Inc (Midland, Mich.) as 15.35% w/w solution in MeOH. All experiments with moisture- and/or air-sensitive compounds are carried out under a dried $N_2$ or Ar atmosphere. For column chromatography, Merck 60 Silica Gel is used (70-230 mesh). Thin-layer chromatography (TLC) is performed on silica gel 60 F-254 plates from EM Reagents. All water used is purified using a Hydro Ultrapure Water Purification system (Rockville, Md.). Isoflurane are obtained from Abbott Laboratories. 3M™ Fluorinert™ Electronic Liquid FC-77 is used in placed of water to maintain the temperature of the mouse at 32±1° C. using a Polyscience Model 210 heating recirculator.

Proton and $^{13}C$ NMR data are obtained using a Varian Gemini 300 MHz instrument and chemical shifts are reported in ppm on the $\delta$ scale relative to TMS, TSP, or residual solvent. Proton chemical shifts are annotated as follows: ppm (multiplicity, coupling constant (Hz), integration). Low and high resolution mass spectra (HRMS) are obtained on a Waters' LCT Premier time-of-flight mass spectrometer using an electrospray ionization (ESI/TOF/MS) in positive ion mode operated at a resolution of 10000. The electrospray capillary voltage was 3 kV and the sample cone voltage is 60V. Desolvation temperature is 225° C. and the desolvation gas is nitrogen at 300 L/hr. Accurate masses are obtained using the lock spray mode with Leu-Enkephalin as the external reference compound. Elemental analyses are performed by Desert Analytics (Tucson, Ariz.) using combustion analysis method for C, H, N and S and inductively coupled plasma-atomic emission spectroscopy (ICP-AES) method for determining the percentage of Gd. MALDI-TOF mass spectral data are obtained by the Scripps Center for Mass Spectrometry (La Jolla, Calif.).

Dendrimer conjugation and purity is assessed by size exclusion HPLC (SE-HPLC) using a Beckman System Gold (Fullerton, Calif.) equipped with model 126 solvent delivery module and a model 168 UV detector ($\lambda$ 254 and 280 nm) controlled by 32 Karat software. Size exclusion chromatography is performed on a Tosohaas G2000SW or a G3000SW, 10 µm, 7.8 mm×30 cm column (Montgomeryville, Pa.) using phosphate buffered saline (1×PBS) solution as the eluent (0.5 mL/min).

Example 1

This example demonstrates a method of synthesis of 2-methyl-6-(p-aminobenzyl)diethylene-N,N,N',N'',N''-penta-tert-butylacetate (2). See FIG. 1.

A solution of aryl nitro compound 1 (1.98 g, 2.41 mmol) in EtOH (30 mL) is treated with 10% Pd/C (0.2 g) and stirred under an $H_2$ atmosphere overnight. The mixture is filtered on a glass frit through a pad of Celite 535 (Fluka) washing with EtOH (2×20 mL). The filtrate is evaporated at reduced pressure to give a pale, yellow oil. The residue is purified by flash chromatography on silica gel eluted with THF-hexanes 1:2 to 1:1 to afford amine 2 (1.81 g, 95%) as a colorless oil.

$^1H$ NMR (DMSO-$d_6$) $\delta$ 6.91 (d, J=8.2 Hz, 2H), 6.53 (d, J=8.5 Hz, 2H), 3.40 (m, 10H), 3.10-2.30 (complicated m, 8H), 1.46 (m, 45H), 0.98 (d, J=6.3 Hz 3H); HRMS: calcd for $C_{42}H_{73}N_4O_{10}$ [M+H$^+$]: 793.5327, found 793.5349.

Example 2

This example demonstrates a method of synthesis of 2-methyl-6-(p-aminobenzyl-N-[5-oxopentanoic acid])diethylene-N,N,N',N'',N'''-penta-tert-butylacetate (3). See FIG. 1.

A solution of 2 (2.10 g, 2.65 mmol) in EtOAc (30 mL) is treated with glutaric anhydride (0.36 g, 3.18 mmol) and stirred at room temperature for 18 h. The solution is evaporated at reduced pressure and the residue is chromatographed on silica gel eluting with EtOH-hexanes 1:4 to 1:1 to yield acid 3 as a colorless solid (1.98 g, 82%).

$^1H$ NMR (DMSO-$d_6$) $\delta$ 10.32 (s, 1H), 7.59 (d, J=8.5 Hz, 2H), 7.15 (d, J=8.5 Hz, 2H), 3.40 (m, 10H), 3.20-2.20 (complicated m, 8H), 2.35 (t, J=7.1 Hz, 2H), 2.12 (t, J=6.9 Hz, 2H), 1.89 (m, 2H), 1.46 (m, 45H), 0.98 d, J=6.3 Hz 3H); HRMS: calcd for $C_{47}H_{79}N_4O_{13}$ [M+H$^+$]: 907.5644, found 907.5645.

Example 3

This example demonstrates a method of synthesis of 2-methyl-6-(p-aminobenzyl-N-[5-oxopentanoic acid])diethylene-N,N,N',N'',N''-penta-tert-butylacetate hydroxysuccinimidyl ester (4). See FIG. 1.

To solution of acid 3 (2.20 g, 2.40 mmol) in MeCN (50 mL) is added EDCI (0.92 g, 4.80 mmol), and N-hydroxysuccinimide (0.41 g, 3.60 mmol). The mixture is stirred at room temperature for 18 h. Afterwards, the reaction solution is concentrated at reduced pressure, diluted with $CH_2Cl_2$ (100 mL), and then washed successively with $H_2O$ (2×100 mL), 5% w/v NaHCO$_3$ (2×100 mL), and $H_2O$ (2×100 mL). The organic layer is dried over anhydrous $Na_2SO_4$ and evaporated to afford active ester 4 as a yellow solid (2.0 g, 83%).

$^1H$ NMR (DMSO-$d_6$) $\delta$ 9.90 (s, 1H), 7.57 (d, J=8.5 Hz, 2H), 7.10 (d, J=8.5 Hz, 2H), 3.40 (m, 10H), 3.20-2.20 (complicated m, 8H), 2.90 (s, 4H), 2.82 (t, J=7.1 Hz, 2H), 2.50 (t, J=6.9 Hz, 2H), 2.08 (m, 2H), 1.45 (m, 45H), 0.98 (d, J=6.9 Hz 3H); HRMS: calcd for $C_{51}H_{82}N_5O_{15}$ [M+H$^+$]: 1004.5807, found 1004.5844.

Example 4

This example demonstrates a method of synthesis of 2-methyl-6-(p-isothiocyanatobenzyl)diethylene-N,N,N',N'',N''-penta-tert-butylacetate (5). See FIG. 1.

A solution of aniline 2 (8.10 g, 10.20 mmol) in EtOAc (30 mL) is treated with thiophosgene (1.52 g, 13.30 mmol) and stirred at room temperature for 4 h. The solution is evaporated under reduced pressure and dried under vacuum to afford 5 as a yellow solid (8.2 g, 98%).

$^1H$ NMR (DMSO-$d_6$) $\delta$ 7.45 (m, 4H), 3.80-2.60 (complicated m, 18H), 1.50 (m, 45H), 1.01 (m, 3H); HRMS: calcd for $C_{43}H_{71}N_4O_{15}S$ [M+H$^+$]: 835.4891, found 835.4880.

Example 5

This example demonstrates a method of synthesis of 2-methyl-6-(p-aminobenzyl-N—[N-maleimidocaproic acid])diethylene-N,N,N',N'',N''-penta-tert-butylacetate (6). See FIG. 1.

To solution of aniline 2 (0.22 g, 0.28 mmol) in $CH_2Cl_2$ (10 mL) is added 1-[3-(dimethylamino)propyl]-3-ethylcarbodiimide hydrochloride (0.12 g, 0.63 mmol), N-$\epsilon$-maleimidocaproic acid (0.06 g, 0.30 mmol). The mixture is stirred at room temperature for 18 h. Afterwards, the reaction solution is diluted with $CH_2Cl_2$ (50 mL), and then washed successively with $H_2O$ (2×50 mL), 5% w/v NaHCO$_3$ (2×50 mL), and $H_2O$ (2×50 mL). The organic layer is dried over anhydrous $Na_2SO_4$, evaporated, and chromatographed on silica gel eluting with EtOH-hexanes 1:4 to 1:1 to yield 6 as a colorless oil (0.23 g, 84%).

$^1H$ NMR (DMSO-$d_6$) $\delta$ 9.82 (s, 1H), 7.55 (d, J=8.1 Hz, 2H), 7.18 (d, J=8.4 Hz, 2H), 7.09 (s, 2H), 3.45 (m, 12H), 3.20-2.40 (complicated m, 8H), 2.32 (t, J=6.9 Hz, 2H), 1.80-1.20 (m, 51H), 1.00 (m, J=6.3 Hz 3H); ES-MS: calcd for $C_{52}H_{84}N_5O_{13}$ [M+H$^+$]: 986.6, found 986.6.

Example 6

Figure 2:
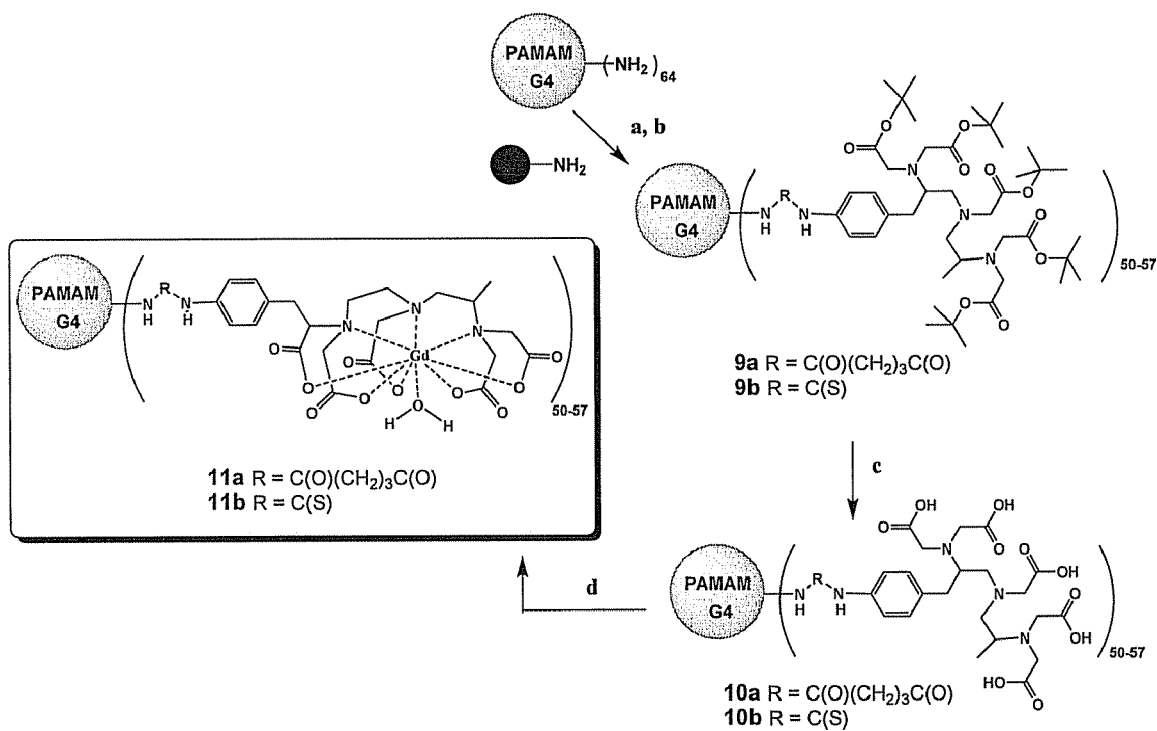
FIG. 2 illustrates a method of preparing Gd-1B4M-DTPA functionalized PAMAM G4 dendrimers, in accordance with an embodiment of the invention. The reaction conditions are: (a) NHS-1B4M-DTPA (4), Et$_3$N, DMSO for 9a; (b) NCS-1B4M-DTPA (5), MeOH for 9b; (c) trifluoroacetic acid; and (d) Gd(OAc)$_3$xH$_2$O, citrate buffer.

This example demonstrates a method of synthesis of 1B4M-DTPA functionalized dendrimer by active ester conjugation (10a) in accordance with an embodiment of the invention. See FIG. 2.

A solution of amine-terminated G4-PAMAM dendrimer (1.34 g of a 15.35% w/w solution in MeOH, 0.01447 mmol) is evaporated in vacuo and washed with hexane (2×10 mL). The residue is dissolved in DMSO (15 mL) and 1B4M-DTPA derivative 4 (1.86 g, 1.85 mmol) is added. The mixture is stirred at room temperature for 24 h, diluted with $CH_2Cl_2$ (15 mL), and then treated with N-(2-aminoethyl)aminomethyl polystyrene (1.0 g, loading: ≧2.00 mmol/g) (NOVA Bio-Chem). The resulting mixture is again stirred for 24 h, filtered, and the filtrate concentrated under reduced pressure to provide crude 9a.

TLC: UV active long band starting from the origin on the silica/aluminum oxide-coated plate using $CHCl_3$-MeOH (9:1) as developing solvents; MALDI/TOF/MS: m/z 49801, calcd for [G4(1B4M-tert-butyl penta-ester)$_{40}$ $C_{2502}H_{4288}N_{410}O_{604}$] 49779).

Crude 9a is then treated with trifluoroacetic acid (20 mL) and stirred for 18 h. The solution is then evaporated, the resulting residue is washed with $CH_2Cl_2$ (2×30 mL), and then dissolved in $H_2O$ (30 mL). The dendrimer solution is adjusted to pH=5 with 1N aqueous NaOH, dialyzed exhaustively with water using a Centriprep Ultracel YM-10 (MWCO 10000 Da) (Millipore), and lyophilized to give a 10a as a white solid (0.51 g, 89.6%).

MALDI/TOF/MS: m/z 39329, cacld for [G4(1B4M)$_{41}$ $(H_2O)_9$, $C_{1729}H_{2742}N_{414}O_{625}$] 39329; Anal. Calcd. for [G4 $(1B4M)_{53}(TFA)_6Na_{40}(H_2O)_{215}$]: C, 47.62; H, 7.18; N, 12.49. found: C, 47.55, 47.75; H, 6.50, 6.56; N, 12.77, 12.73; SE-HPLC: a single, symmetric peak with retention time at 12.4 min.

Example 7

This example demonstrates a method of synthesis of 1B4M-DTPA functionalized dendrimer by isothiocyanate conjugation (10b). See FIG. 2.

MeOH (15 mL) and 1B4M-DTPA derivative 5 (1.00 g, 1.20 mmol) are added to a solution of amine-terminated G4-PAMAM dendrimer (0.87 g of a 15.35% w/w solution in MeOH, 0.00935 mmol). The mixture is stirred at room temperature for 24 h, evaporated, diluted with $CH_2Cl_2$ (15 mL), and then treated with N-(2-aminoethyl)-aminomethyl polystyrene (0.6 g, loading: ≧2.00 mmol/g). The resulting mixture is again stirred for 24 h, filtered, and the filtrate concentrated under the reduced pressure to afford crude 9b.

TLC: UV active long band starting from the origin on the silica/aluminum oxide-coated plate using $CHCl_3$-MeOH (9:1) as developing solvents; MALDI/TOF/MS: m/z 42014, calcd for [G4(1B4M-tert-butyl penta-ester)$_{33}$, $C_{2041}H_{3558}N_{382}O_{454}S_{33}$] 41773.

The residue 9b is then treated with trifluoroacetic acid (10 mL) and stirred for 18 h. The solution is then evaporated and the resulting residue is washed by $CH_2Cl_2$ (2×30 mL) and dissolved in $H_2O$ (30 mL). The dendrimer solution is adjusted to pH=5 with 1N aqueous NaOH, dialyzed exhaustively with water using Centriprep Ultracel YM-10 (MWCO 10000 Da), and lyophilized to give 10b as a yellow solid (0.31 g, 66.4%).

MALDI/TOF/MS: m/z 28403, calcd for [G4(1B4M)$_{25}$ $(H_2O)_{18}$, $C_{1197}H_{2034}N_{350}O_{392}S_{25}$] 28403; Anal. Calcd. for [G4(1B4M)$_{50}$(TFA)$_5$Na$_{25}$(H$_2$O)$_{80}$]: C, 48.07; H, 6.60; N, 14.17; S, 3.60. found: C, 48.93, 48.48; H, 6.65, 6.50; N, 14.51, 14.47; S, 1.06, 1.36; SE-HPLC: a single, symmetric peak with retention time at 12.7 min.

Example 8

This example demonstrates a general procedure of Gd complexation to the dendrimer-1B4M conjugate.

Gadolinium acetate ($Gd(OAc)_3 \cdot xH_2O$) is added to a solution of dendrimer-1B4M-DTPA (150 mg) in 0.3M citrate buffer (10 mL, pH=4.5). The amount of gadolinium acetate used is calculated to be a 1.5 times molar excess based on the number of 1B4M units conjugated to the dendrimer. The solution is stirred at room temperature for 12 h and then dialyzed exhaustively with water using a Centriprep Ultracel YM-10 (MWCO 10,000 Da) and monitored by SE-HPLC. The retentate is lyophilized, and the product is obtained as a yellow solid.

Example 9

Figures 5A, 5B:
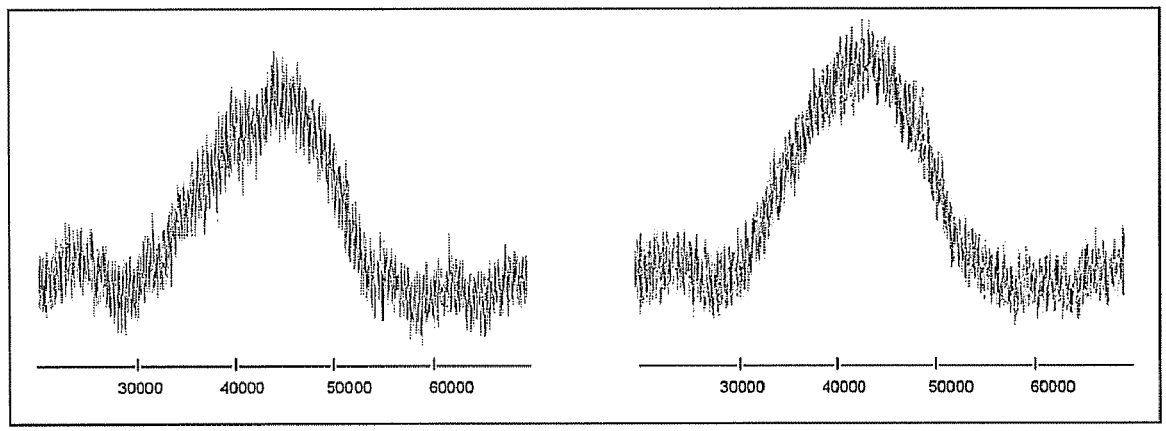
FIG. 5A is a MALDI/TOF mass spectrum of macromolecular conjugate ligand complex 11a, and FIG. 5B is a MALDI/TOF mass spectrum of macromolecular conjugate ligand complex 11b, in accordance with an embodiment of the invention.

This example demonstrates a structural characterization of Gd-1B4M-DTPA functionalized dendrimer by active ester conjugation (11a) as described in Example 9. See FIGS. 2 and 5.

MALDI-TOF-MS: m/z 44326 (see FIG. 5), cacld for [G4 (Gd-1B4M)$_{39}$(H$_2$O)$_{25}$, $C_{1675}H_{2505}Gd_{39}N_{406}O_{616}$]: 44318; Anal. Calcd. for [G4(1B4M)$_{53}$Gd$_{36}$(C$_6$H$_7$O$_3$)$_{15}$Na$_{45}$ (H$_2$O)$_{110}$]: C, 44.35; H, 6.04; N, 11.16; Gd, 9.76. found: C, 44.53, 44.18; H, 5.79, 5.76; N, 11.34, 11.29; Gd, 9.57, 10.00; SE-HPLC: a single, symmetric peak with retention time at 12.4 min.

Example 10

This example demonstrates a structural characterization of Gd-1B4M-DTPA functionalized dendrimer by isothiocyanate conjugation (11b) as described in Example 9. See FIGS. 2 and 5.

MALDI-TOF-MS: m/z 43312 (see FIG. 5), calcd for [G4 (Gd-1B4M)$_{41}$(H$_2$O)$_7$, $C_{1565}H_{2287}Gd_{41}N_{414}O_{541}S_{41}$]: 43318; Anal. Calcd. for [G4(1B4M)$_{57}$Gd$_{41}$(C$_6$H$_7$O$_3$)$_8$Na$_{50}$ (H$_2$O)$_{170}$]: C, 41.08; H, 5.63; N, 11.57; S, 3.16; Gd, 11.14. found: C, 41.23, 41.11; H, 5.48, 5.48; N, 11.18, 11.18; S, 2.19, 1.96; Gd, 12.13, 11.28; SE-HPLC: a single, symmetric peak with retention time at 12.7 min.

Example 11

Figure 3:
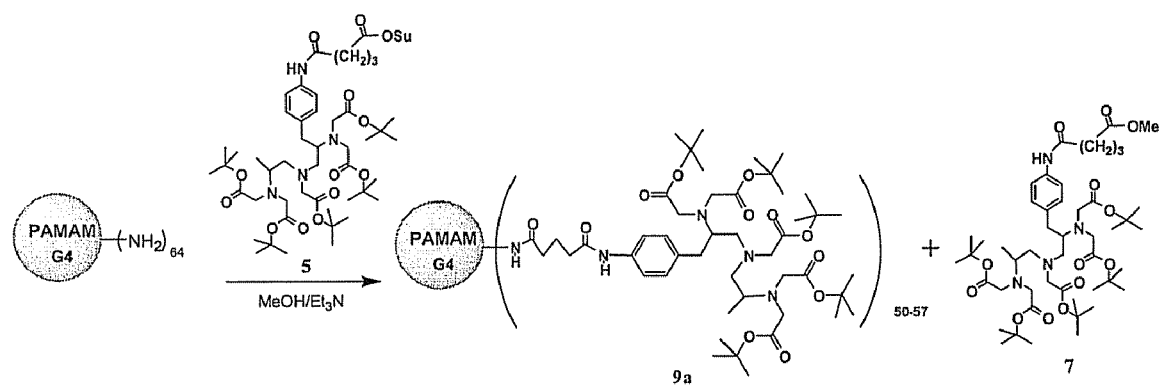
FIG. 3 illustrates a method of preparing 2-methyl-6-(p-aminobenzyl-N-[5-oxopentanoic acid])diethylene-N,N,N',N'',N'''-penta-tert-butylacetate methyl ester (7), which is a precursor to a compound in accordance with an embodiment of the invention.

This example demonstrates a structural characterization of 2-methyl-6-(p-aminobenzyl-N-[5-oxopentanoic acid])diethylene-N,N,N',N'',N''-penta-tert-butylacetate methyl ester (7). See FIG. 3.

To a solution of amine-terminated G4-PAMAM dendrimer (0.09 g of a 15.35% w/w solution in MeOH, 0.00094 mmol) are successively added MeOH (30 mL) and 1B4M-DTPA derivative 5 (0.12 g, 0.12 mmol) and Et$_3$N (0.02 mL, 0.12 mmol). The mixture is stirred at room temperature for 24 h and then concentrated under reduced pressure to afford the desired product 9a and by-product 7. Methyl ester 7 was isolated by preparative silica-coated TLC plate eluting with hexane/EtOAc (1:2) (25 mg, 25%).

$^1$H NMR (DMSO-d$_6$) δ 9.88 (s, 1H), 7.55 (d, J=8.1 Hz, 2H), 7.19 (d, J=6.9 Hz, 2H), 3.69 (s, 3H), 3.42 (m, 101H), 3.20-2.20 (complicated m, 12H), 1.90 (m, 2H), 1.45 (m, 45 H), 1.00 (d, J=6.9 Hz 3H); ES-MS: calcd for $C_{48}H_{81}N_4O_{13}$ [M+H$^+$]: 821.5800, found 821.5790.

Example 12

Figure 4:
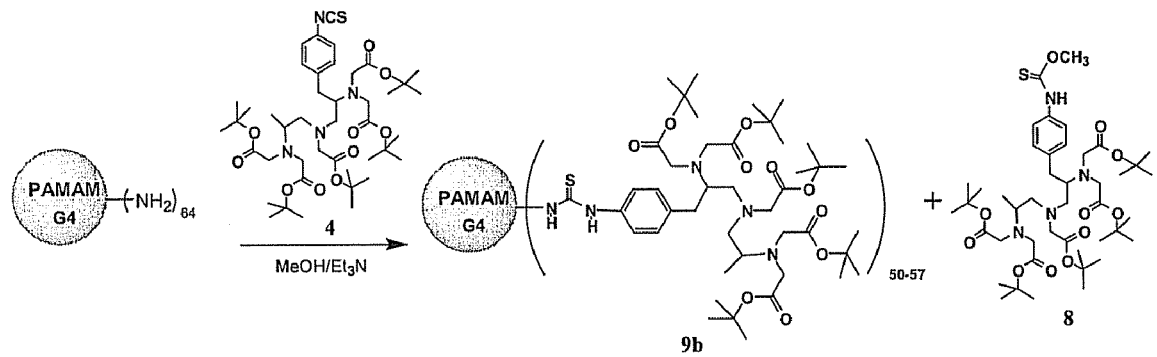
FIG. 4 illustrates a method of preparing 2-methyl-6-(p-methylisothiourethanebenzyl)diethylene-N,N,N',N'',N'''-penta-tert-butylacetate (8), which is a precursor to a compound in accordance with an embodiment of the invention.

This example demonstrates a structural characterization of 2-methyl-6-(p-methylisothiourethanebenzyl)diethylene-N,N',N'',N'''-penta-tert-butylacetate (8). See FIG. 4.

To a solution of amine-terminated G4-PAMAM dendrimer (0.44 g of a 15.35% w/w solution in MeOH, 0.0047 mmol) are successively added MeOH (15 mL) and 1B4M-DTPA derivative 4 (0.50 g, 0.60 mmol) and Et$_3$N (0.09 mL, 0.60 mmol). The mixture is stirred at room temperature for 24 h, evaporated, diluted with CH$_2$Cl$_2$ (15 mL), and then treated with N-(2-aminoethyl)-aminomethyl polystyrene (0.3 g, loading: ≧2.00 mmol/g). The resulting mixture is again stirred for 24 h, filtered, and the filtrate is concentrated under reduced pressure to afford crude desired product 9b and by-product 8. The methylisothiourethane 8 is isolated by flash chromatograph on aluminum oxide eluting with hexane/EtOAc (3:1-1:2)(40 mg, 7.7%).

$^1$H NMR (DMSO-d$_6$) δ 11.20 (s, 1H), 7.30 (m, 4H), 4.00 (s, 311), 3.80-3.00 (complicated m, 18H), 1.45 (s, 45H), 1.00 (d, J=6.9 Hz 3H); HRMS: calcd for C$_{44}$H$_{75}$N$_4$O$_{11}$ [M+H$^+$]: 867.5153, found 867.5164.

Example 13

This example demonstrates a method of synthesis of G4-1B4M$_{60}$-Gd$_{42}$ (Yordanov et al., *J. Mater. Sci. Chem.*, 2003, 13, 1523-1525).

PAMAM dendrimer (10% solution in MeOH, Aldrich) (70 μmole) is added to a bicarbonate buffer solution (pH 8.5). The bifunctional chelate, p-SCN-1B4M-DTPA, (14 mmole) is added to dendrimer solution as a solid in portions during a course of a week. The mixture is stirred at room temperature for 14 days, while the pH is maintained at 8.5 by addition of 5% aqueous NaHCO$_3$. On the 14th day, the reaction mixture is heated at 30° C. for another 24 h.

The reaction solution is transferred into a 250 mL Amicon diafiltration cell (Millipore) with a 10 kDa cut-off membrane (Millipore) and subjected to an exhaustive diafiltration with deionized water until no chelate is detected in the filtrate by SE-HPLC. The residual solution is lyophilized and the dendrimer-1B4M conjugate is obtained as an off-white solid (~90% yield based on dendrimer).

Compound 12 (precursor to G4-1B4M$_{60}$-Gd$_{42}$): Anal. Calcd. for G4.(B134M)$_{60}$Na$_{138}$(HCO$_3$)$_5$(H$_2$O)$_{75}$ [(C$_{622}$H$_{1248}$N$_{250}$O$_{124}$)(C$_{23}$H$_{26}$N$_4$O$_{10}$S)$_{60}$Na$_{138}$(HCO$_3$)$_5$ (H$_2$O)$_{75}$]: C, 45.93; H, 6.15; N, 13.09; S, 3.67. Found: C, 46.88, 46.49; H, 5.61, 5.60; N, 12.92, 12.88; S, 2.23, 2.60. MALDI-TOF (THAP): m/z for SE-HPLC: R$_t$ 12.7 min.

A slight excess of Gd(OAc)$_3$ (0.1 mmol in excess) in 0.3 M citrate buffer (pH=4.5) is added to a solution of 12 in the same buffer. The solution is stirred at room temperature for 15 h and then transferred into a 250 mL diafiltration cell with a 10 kDa cut-off membrane. The solution is subjected to an exhaustive diafiltration with deionized water and monitored by SE-HPLC. The retentate is lyophilized, and the product is obtained as an off-white solid (87% yield based on dendrimer 12). Low yield is attributed to the formation of aggregates and loss during the dialfiltration process.

Compound G4-1B4M$_{60}$-Gd$_{42}$: Anal. Calcd. for G4.(1B4M)$_{60}$Gd$_{42}$Na$_{125}$(C$_6$H$_7$O$_7$)$_{10}$(H$_2$O)$_{60}$ [(C$_{622}$H$_{1248}$N$_{250}$O$_{124}$)(C$_{23}$H$_{26}$N$_4$O$_{10}$S)$_{60}$Gd$_{42}$Na$_{125}$ (C$_6$H$_7$O$_7$)$_{10}$(H$_2$O)$_{60}$]: C, 41.29; H, 5.44; N, 11.45; S, 3.21; Gd, 11.02. Found: C, 41.20, 42.41; H, 4.83, 4.63; N, 12.22, 11.87; S, 2.09, 2.05; Gd, 11.33, 10.99. MALDI-TOF (THAP): m/z for SE-HPLC R$_t$ 11.5, 12.6 min.

Example 14

This example demonstrates certain properties of the macromolecular conjugated metal complexes in accordance with an embodiment of the invention.

Solutions of compounds 11a and 11b (0.25-1.0 mM) in 1×PBS (300 μL volume) are prepared along with a corresponding set from the G4-1B4M$_{60}$-Gd$_{42}$ (Example 13) prepared by aqueous chemistry for comparison purposes. Measurements are obtained at ~22° C. using a 3-Tesla clinical scanner (Signa Excite, General Electric Medical System, Waukesha, Wis.) equipped with a rectangular single loop receiver coil (84×126×6 mm). Images of the solutions using an 8-echo 2D-spin echo (2D-SE) sequence are acquired with repetition times of 167, 300, 617, 1250, 2500 and 5000 ms at echo time of 9.2 ms. T$_1$ and T$_2$ maps are calculated using ImageJ MRI Analysis plug-in (http://rsb.info.nih.gov/ij/plugins/mri-analysis.html). T$_1$ and T$_2$ relaxivities, R$_1$ and R$_2$, are determined from the slopes of the plot of relaxation rates, R$_1$=1/T$_1$ and R$_2$1/T$_2$, vs [Gd]. The results are summarized in Table 1.

TABLE 1

| Compound | Number of Chelates[a] | Saturation Percentage | T$_1$ relaxivity mM$^{-1}$s$^{-1}$[b] | T$_2$ relaxivity mM$^{-1}$s$^{-1}$[c] |
|---|---|---|---|---|
| 10a | 53 | 83 | ND | ND |
| 10b | 50 | 78 | ND | ND |
| 11a | 50 | 78 | 12.2 ± 0.6 | 24.9 ± 0.5 |
| 11b | 57 | 89 | 14.2 ± 1.4 | 34.5 ± 2.1 |
| G4-1B4M$_{60}$-Gd$_{42}$ | 60 | 94 | 13.9 ± 1.6 | 33.6 ± 3.1 |

[a]Reported values are the average values as calculated from the within 0.6% of the elemental analyses (C, H, N, S, and Gd) results which can be ± 10 of the mean value of the reported # of chelates, and ± 5 of the #Gd.
[b]T$_1$ molar relaxivity values obtained from phantom measurements. Errors are reported as standard deviations.
[c]T$_2$ molar relaxivity values obtained from phantom measurements. Errors are reported as standard deviations.
ND = not determined.

Example 15

This example demonstrates dynamic contrast-enhanced MR angiography imaging experiments.

All procedures are performed in accordance with the National Institutes of Health guidelines on the use of animals in research and are approved by the Animal Care and Use Committee of the National Cancer Institute.

Normal 6-8 weeks old athymic nu/nu mice (Charles Rivers Laboratories) are imaged in pairs to increase throughput on a 3-Tesla clinical scanner (Philips Intera 3.0T, Philips Medical System, Best, The Netherlands) using a parallel receiver coil array compromised of two modified Alderman-Grant resonators (38 mm OD×75 cm) and equipped with a multi-channel animal support and monitoring system. Mice (n=4 per agent evaluated) are anesthetized with 2.5% Isoflurane (Abbott Laboratories, N.J.) in O$_2$ delivered using a Summit Anesthesia Solutions vaporizer (Bend, Oreg.) at a O$_2$ flow rate of 1.0 L/min. Respiration rate is kept at 25-30 respirations per min and monitored using a Biopac System MP150 (Biopac Inc., Goleta, Calif.). 3M™ Fluorinert™ Electronic Liquid FC-77 is used in place of water to maintain the temperature of the mouse at 32±1° C. using a Polyscience Model 210 heating recirculator while the mouse body temperature is monitored using FOT-M fiber optic temperature sensors (Fiso Technologies Inc., San Jose, Calif.) with a UMI-8 Universal Multi-channel Instrument (Fiso Technologies Inc.) Prior to contrast agent injection, a $T_1$ map is obtained by using a 3D-fast spoiled gradient echo image (3D-fSPGR) sequence at two different flip angles (repetition time/echo time 8.8/1.9 ms; flip angles 8° and 24°; bandwidth 31.25 kHz; matrix size 512×128×40; voxel resolution 156×156×600 μm; 4 excitations; scan time 4 min 29 sec). A 100 μL total volume consisting 50 μL of 12 mM Gd (dose of 0.03 mmole Gd/kg mouse) and 50 μL of 1×PBS is injected in the tail vein of each mouse at a rate of 150 μL/min through 30-gauge needles attached to Tygon tubing (0.010 in id×10 m length) using dual 1.0 cc syringes in a Harvard Apparatus PHD2000 (Holliston, Mass.) syringe pump. Dynamic MR angiography images are obtained immediately after injection by repeating the 3D-fSPGR sequence at the higher flip angle every 5 minutes for 1 h.

The dynamic 3D images are processed using ImageJ (http://rsb.info.nih.gov/ij/plugins/mri-analysis.html). The baseline pre-contrast 3D images are subtracted from each of the post-contrast 3D images and a maximum intensity projection (MIP) is calculated of the resulting 3D images. The resulting MIP images are subjectively compared by a board certified radiologist (PC) and an MR physicist (MB) for image clarity and for opacification of vessels and organs.

Time curves for clearance from the blood are measured from an ROI that is drawn over the jugular vein using ImageJ (http://rsb.info.nih.gov/ij/) and exported for analysis to Igor Pro (Wavemetrics, Inc., Lake Oswego, Oreg.). The clearance rates are determined by fitting the decay curves to a single exponential decay function with the baseline fixed to zero and clearance pseudo-first order rate constants are calculated (Table 2). Results are averaged for all animals in each group ($n \geq 4$). The statistical analysis of the differences between clearance rates and relaxivity values among the three agents is assessed with a student's t-test using an Excel spreadsheet (Microsoft, Redmond, Wash.).

TABLE 2

Blood Clearance Rates

| Compound | $10^3 k_{obs}$, 1/min[a] | half life, min[b] |
|---|---|---|
| 11a | 8.012 ± 0.766 | 87.10 ± 8.15 |
| 11b | 11.885 ± 2.594 | 60.29 ± 11.47 |
| G4-1B4M$_{60}$-Gd$_{42}$ | 16.295 ± 1.994 | 43.07 ± 5.40 |

[a]Calculated pseudo-first order rate constant according to the equation $[Gd]_t = [Gd]_0 e^{-kt}$ as measured from the R1 map of the jugular vein.
Errors are reported as standard deviations.
[b]Calculated half life from the first order rate constant $t_{1/2} = \frac{0.693}{K_{obs}}$.

Errors are reported as standard deviations.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of preparing a macromolecular conjugated ligand comprising:
   (a) providing a compound of formula (I)

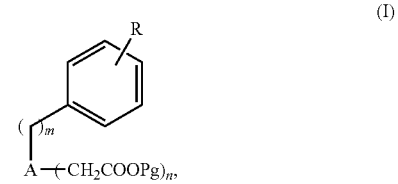

(I)

wherein
-A-(CH$_2$COOPg)$_n$ is a group of the formula (III)

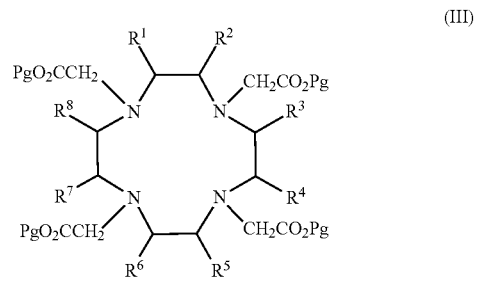

(III)

wherein each of $R^1$-$R^8$ is the same or different and is hydrogen, a $C_1$-$C_{12}$ alkyl group, or a point of attachment of

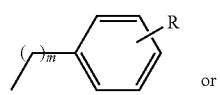

or wherein $R^1$ and $R^2$ and/or $R^3$ and $R^4$ together form a $C_5$-$C_7$ cycloalkyl group, R is

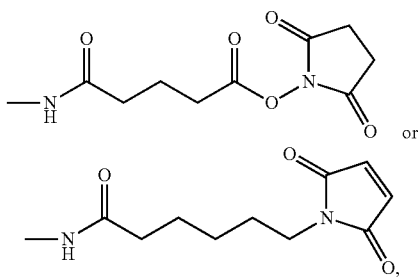

or

Pg is a carboxyl-protecting group,
and m is 0 to 3,
(b) reacting the compound of formula (I) with a macromolecular compound in an organic solvent medium which is substantially free of water to obtain a carboxyl-protected macromolecular conjugated ligand, and
(c) removing the carboxyl-protecting group to obtain a macromolecular conjugated ligand.

2. The method of claim 1, further comprising step (d), wherein step (d) comprises reacting the macromolecular conjugated ligand with an ion, which is optionally radioactive, to obtain a macromolecular conjugated ligand complex.

3. The method of claim 1, wherein -A–(CH$_2$COOPg)$_n$ is

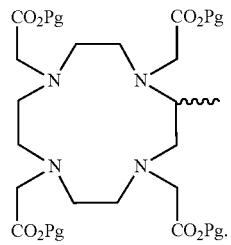

4. The method of claim 2, wherein the ion is a metal ion.

5. The method of claim 1, wherein Pg is selected from the group consisting of alkyl, benzyl, 9-fluorenylmethyl, diphenylmethyl, silylalkyl, haloalkyl, and 1,1-dimethylallyl (DMA).

6. The method of claim 1, wherein the macromolecular compound is a biomolecule.

7. The method of claim 1, wherein the macromolecular compound is a dendrimer.

8. The method of claim 7, wherein the dendrimer is polyamidoamine (PAMAM).

9. The method of claim 8, wherein the PAMAM is of generation 4 (G4).

10. The method of claim 1, wherein Pg is alkyl.

11. The method of claim 10, wherein the alkyl is t-butyl.

12. The method of claim 1, wherein the organic solvent medium comprises one or more organic solvents selected from the group consisting of alkanes, nitriles, aromatic hydrocarbons, haloalkanes, alcohols, amides, alkylesters, sulfoxides, cycloalkanes, dialkylethers, alkyl aryl ethers, diarylethers, and cyclic ethers, or any combination thereof.

13. The method of claim 1, wherein the organic solvent medium is selected from the group consisting of acetonitrile, dimethylformamide (DMF), benzene, methylene chloride, methanol, hexane, dimethylsulfoxide (DMSO), tetrahydrofuran (THF), furan, diphenyl ether, diethyl ether, methylethyl ether, and dioxane, and any combination thereof.

14. The method of claim 1, wherein the organic solvent medium is methanol or DMSO.

15. The method of claim 1, wherein the organic solvent medium is DMSO.

16. The method of claim 2, wherein the ion is selected from the group consisting of Ac, Bi, Pb, Y, Mn, Cr, Fe, Co, Ni, Tc, In, Ga, Cu, Re, a lanthanide ion, and an actinide ion.

17. The method of claim 2, wherein the ion is Gd(III), $^{111}$In, [86]Y, or a lanthanide ion.

18. The method of claim 1, wherein in step (c), the carboxyl-protecting group is removed by the addition of an acid.

19. The method of claim 1, wherein R is

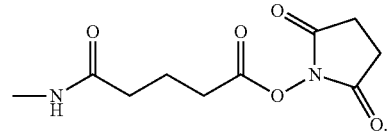

20. A compound of formula
formula (Ie):

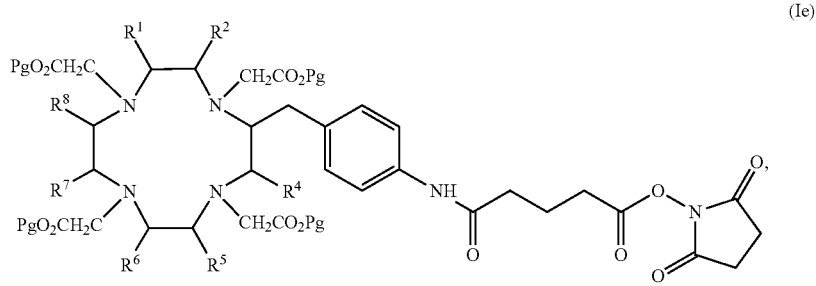

and
formula (If):

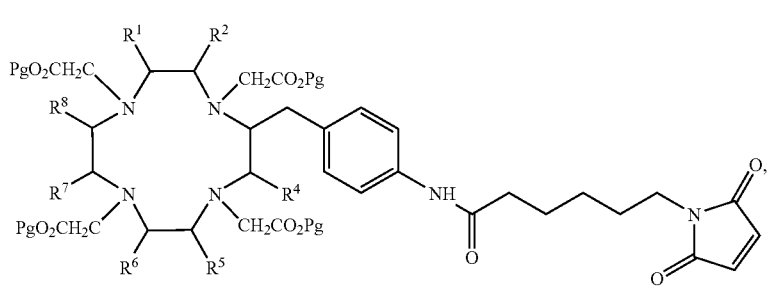

wherein
Pg is a carboxyl-protecting group, and
R$^1$, R$^2$, and R$^4$-R$^8$ are the same or different and each is hydrogen or a C$_1$-C$_{12}$ alkyl group, or R$^1$ and R$^2$ together form a C$_5$-C$_7$ cycloalkyl group.

21. The compound of claim 20, wherein Pg is selected from the group consisting of alkyl, benzyl, 9-fluorenylmethyl, diphenylmethyl, silylalkyl, haloalkyl, and 1,1-dimethylallyl (DMA).

22. The compound of claim 20, wherein Pg is alkyl.

23. The compound of claim 20, wherein the alkyl is t-butyl.

24. The method of claim 1, wherein R is

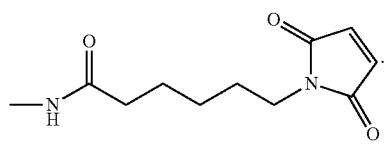

25. The method of claim 1, wherein the compound of formula (I) is of the formula formula (Ie):

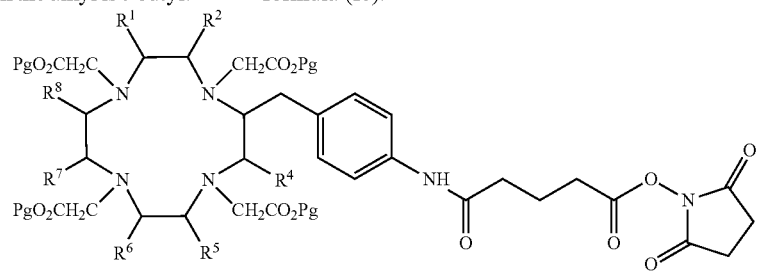

and
formula (If):

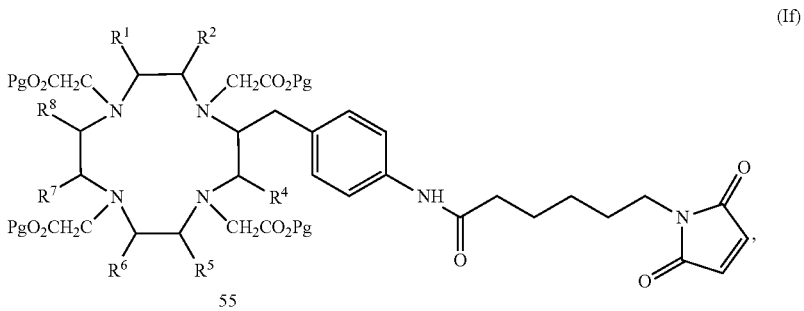

wherein
Pg is a carboxyl-protecting group, and
R$^1$, R$^2$, and R$^4$-R$^8$ are the same or different and each is hydrogen or a C$_1$-C$_{12}$ alkyl group, or R$^1$ and R$^2$ together form a C$_5$-C$_7$ cycloalkyl group.

26. The compound of claim 25, wherein Pg is selected from the group consisting of alkyl, benzyl, 9-fluorenylmethyl, diphenylmethyl, silylalkyl, haloalkyl, and 1,1-dimethylallyl (DMA).

27. The compound of claim 25, wherein Pg is alkyl.

28. The compound of claim 27, wherein the alkyl is t-butyl.

* * * * *